United States Patent [19]
Broadwin et al.

[11] Patent Number: 5,015,227
[45] Date of Patent: May 14, 1991

[54] APPARATUS FOR PROVIDING ENHANCED TISSUE FRAGMENTATION AND/OR HEMOSTASIS

[75] Inventors: Alan Broadwin, Brooklyn, N.Y.; Joseph N. Logan, Trumbull, Conn.; Peter J. Kuhl, Queens, N.Y.

[73] Assignee: Valleylab Inc., Boulder, Colo.

[21] Appl. No.: 504,453

[22] Filed: Apr. 3, 1990

Related U.S. Application Data

[63] Continuation-in-part of Ser. No. 103,022, Sep. 30, 1987, Pat. No. 4,931,047.

[51] Int. Cl.$^5$ .................. A61B 17/32; A61B 17/39
[52] U.S. Cl. ........................... 604/22; 604/35; 606/42; 606/45; 606/49; 606/169; 200/505; 200/511
[58] Field of Search ............... 604/22, 35; 128/24 A; 606/42, 45, 48–50, 169–171; 200/505, 511

[56] References Cited

U.S. PATENT DOCUMENTS

| 2,714,890 | 8/1955 | Vang | 128/24 A |
|---|---|---|---|
| 3,589,363 | 6/1971 | Banko et al. | 128/24 A |
| 3,636,943 | 1/1972 | Balamuth | 128/24 A |
| 3,693,613 | 9/1972 | Kelmen | 128/24 A |
| 3,815,604 | 6/1974 | O'Malley et al. | 604/22 |
| 4,063,557 | 12/1977 | Wuchinich et al. | 128/24 A |
| 4,378,801 | 4/1983 | Oosten | 606/37 |
| 4,492,832 | 1/1985 | Taylor | 606/42 X |
| 4,552,143 | 11/1985 | Lottick | 606/42 |
| 4,562,838 | 1/1986 | Walker | 606/42 |
| 4,674,498 | 6/1987 | Stasz | 606/48 |
| 4,747,820 | 5/1988 | Hornlein et al. | 604/22 |
| 4,750,902 | 6/1988 | Wuchinich et al. | 604/22 |

FOREIGN PATENT DOCUMENTS

| 2460481 | 6/1976 | Fed. Rep. of Germany | 606/42 |
|---|---|---|---|
| 87/01276 | 3/1987 | PCT Int'l Appl. | |
| 87/06116 | 10/1987 | PCT Int'l Appl. | |

Primary Examiner—Lee S. Cohen
Attorney, Agent, or Firm—Peter C. Richardson; Lawrence C. Akers; Mark Dryer

[57] ABSTRACT

An improved device for delivering RF current to the operating tool of an ultrasonic surgical apparatus which comprises a switch module for selecting said RF current, an electrically conducting metal band connected to the switch module and an electrically conductive O-ring in electrical contact with the metal band and located around the acoustic conecting member of the apparatus.

4 Claims, 1 Drawing Sheet

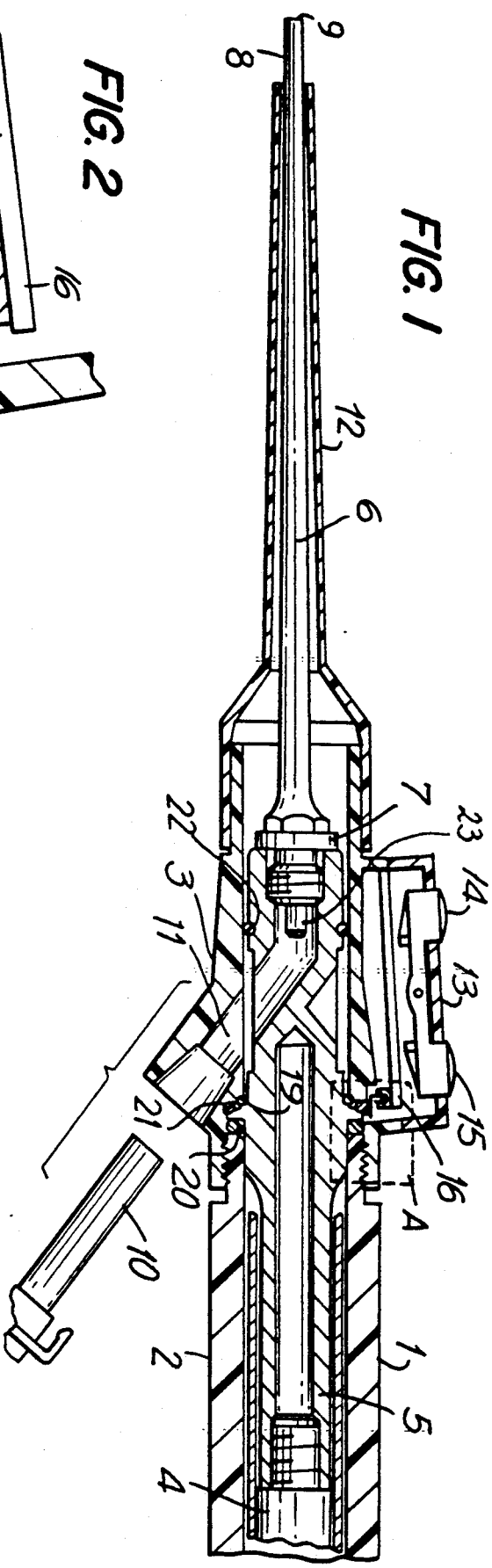
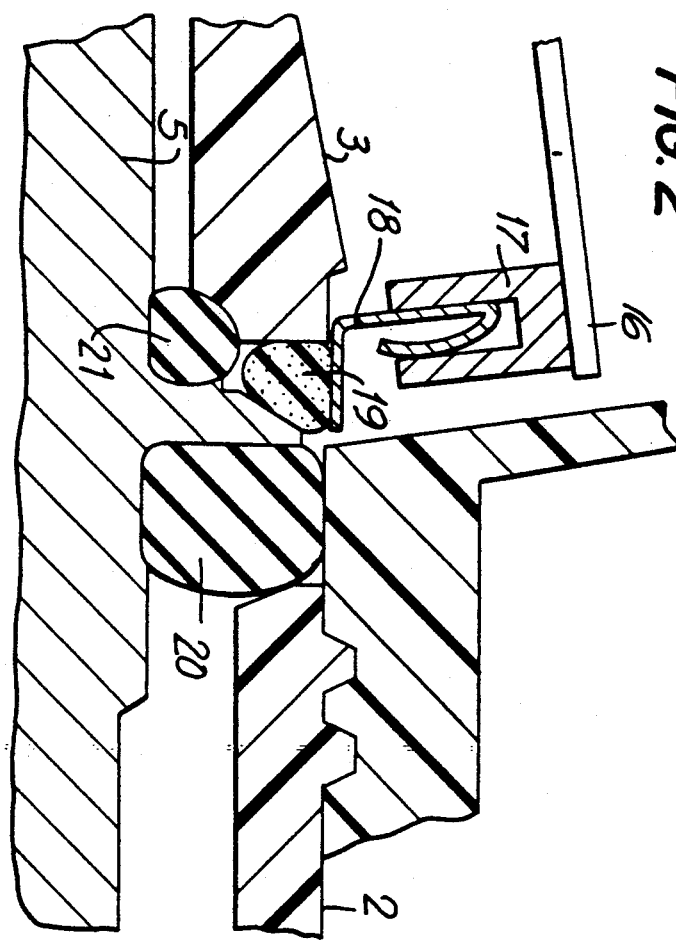
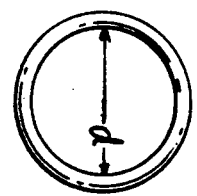

APPARATUS FOR PROVIDING ENHANCED TISSUE FRAGMENTATION AND/OR HEMOSTASIS

BACKGROUND OF THE INVENTION

This is a continuation-in-part of patent application Ser. No. 103,022 filed Sept. 30, 1987 now U.S. Pat. No. 4,931,047.

The present invention relates to a surgical apparatus for ultrasonically fragmenting and aspirating, and electrosurgically coagulating and electrosurgically cutting tissue at an operative site on a patient.

The application of ultrasonically vibrating surgical devices for fragmenting and removing unwanted tissue with precision and safety has led to the development of valuable surgical procedures, and the use of ultrasonic aspirators for the fragmentation and surgical removal of tissue from a body has become well known! Initially, the technique of surgical aspiration was applied for the fragmentation and removal of cataract tissue as shown, for example, in U.S. Pat. Nos. 3,589,363 and 3,693,613; the disclosure in these patents and each of the other patents and documents mentioned herein are hereby incorporated by reference in their entirety. Later, such techniques were applied with significant success to neurosurgery and other surgical specialties where the application of ultrasonic energy through a small, hand-held device for selectively removing tissue on a layer-by-layer basis with precise control has proven feasible.

Certain devices known in the art characteristically produce continuous vibrations having a substantially constant amplitude at a frequency of about twenty to about thirty KHz up to about forty to about fifty KHz. U.S. Pat. No. 3,589,363 describes one such device which is especially adapted for use in the removal of cataracts, while U.S. Pat. No. 4,063,557 describes a device suitable for removal of soft tissue which is particularly adapted for removing highly compliant elastic tissue mixed with blood. Such devices are continuously operative when the surgeon wishes to fragment and remove tissue, and generally operate under the control of a foot switch.

One known instrument for ultrasonically fragmenting tissue at an operative site and then aspirating the tissue particles and fluid away from the site is the CUSA Model System 200 ultrasonic Aspirator which is manufactured and sold by Valleylab, Inc. of Stamford, Conn.; see also U.S. Pat. No. 4,827,911. When the longitudinally oscillating metallic tip in such an aspirator is brought into contact with tissue it gently, selectively and precisely fragments and removes the tissue. Some of the advantages of this unique surgical instrument are that there is little resulting damage to healthy tissue in a tumor removal procedure, blood vessels can be skeletonized, healing of tissue is promoted, no charring or tearing of margins of surrounding tissue results, only minimal pulling of healthy tissue is experienced, and excellent tactile feedback for selectively controlled tissue fragmentation and removal is provided.

Surgeons using the CUSA ultrasonic surgical instrument have indicated a desire for additional and improved capabilities for this instrument. In particular they have requested provisions for controlled penetration of capsular membranes without damage to the organs, precise and rapid removal of fibrous tissue structures such as in mucosal proctectomy procedures, and an increased rate of tissue fragmentation and removal. During many surgical procedures wherein ultrasonic fragmentation instruments have been employed additional instruments have been required for tissue cutting and hemostasis at the surgical site. Hemostasis is needed for example in desiccation techniques for deep coagulation to dry out large volumes of tissue and also in fulguration techniques for spray coagulation to dry out the surfaces of tissues. See, for example, U.S. Pat. No. 4,378,801. Often an electrosurgical pencil plugged into an electrosurgical unit for tissue cutting and hemostasis and a suction prob for aspiration of fluids and tissue particles are used. Since many surgical tools are thereby required at a single surgical site, the total surgical time is increased and efficiency decreased, as the surgeon must switch among different instruments. Also, undesirable amounts of blood are lost because of the time needed to switch from a cutting or fragmenting tool to a cauterizing instrument when bleeding is observed. Additionally, by simultaneously maintaining a plurality of surgical devices at the operative site the surgeon's field of view is reduced. Furthermore, due to the complexity of the procedures, false activation of the electrosurgical pencil, when not in use, can occur, thereby causing RF burning of the patient.

Accordingly a need has arisen for an improved surgical procedure and apparatus which remedies these problems, and meets the above-expressed desires and needs of the surgeons.

The invention disclosed in patent application Ser. No. 103,022, the entire disclosure of which is incorporated herein by reference, remedies these problems by incorporating RF coagulating and RF cutting capabilities to the vibratable tip of an ultrasonic fragmenting and aspiration device.

Thus, Ser. No. 103,022 provides a surgical apparatus for performing one or more surgical procedures at a surgical site on a patient comprising: a handpiece; a tool supported by said handpiece; said tool having a vibrating tool tip; an RF current means selectively operable for providing an RF current to said tool tip for allowing performance of an electrosurgical procedure at the surgical site; a vibrating means for ultrasonically vibrating said tool tip; said tool tip having a tip opening; said tool having a tool passageway therethrough communicating with said tip opening; and an aspirating means for applying a suction pressure on said tool passageway for aspirating tissue particles and fluid at the surgical site through said tip opening through said tool passageway and away from the surgical site, said RF current means including a switching means for switching the RF current provided to said tool tip to at least an RF cutting current during ultrasonic vibration.

Surprisingly, by using the above apparatus the fragmentation and aspiration capabilities are actually enhanced by the delivery of RF energy to the fragmentation and aspiration tip. A switching mechanism conveniently accessible to the surgeon allows him during surgery and with the instrument tip at the surgical site to instantly switch among the application of no active function, one active function, or the simultaneous application of any combination of active functions of the instrument, thereby increasing the efficacy of the instrument and decreasing the time of the surgery. The bleeding which occurs during tissue fragmentation is more quickly and better controlled. There is also provision for controllable delivery of irrigation and cooling fluids to the surgical site The preferred switching means for switching the RF current to the tool tip in the apparatus of Ser. No. 103,022 includes a metallic electrical contact in the form of a thin metal strip which makes touching contact with the electrically conducting metal connecting member attached to the tool. Although this arrangement works well when the instrument is new, since the connecting member undergoes constant vibration when the instrument is in use, it has been found that a certain amount of arcing is unavoidable and this causes erosion and/or build-up of an oxide coating on the metal contact strip or the connecting member or both, and such deterioration leads to increased electrical resistance and interference with the electronic circuitry, resulting in reduced efficiency.

Surprisingly, it has now been found that an effective non-arcing electrical contact can be made and the above effect eliminated by making the electrical contact from the switch to the acoustic connecting member through a conductive O-ring connected to the switch module through a metal contact band. Since the O-ring is located around the acoustic member and is resilient enough to expand and contract with the ultrasonic vibrations, it remains in constant contact with the member and, therefore, is not subject to arcing. It is known that a component which is not transparent to RF waves may be used as a shield in electronic circuits and, traditionally, conductive O-rings of the type contemplated for the present invention have been used in such applications. Conductive O-rings heretofore have been used as a current carrying component in an electronic circuit. However conductive O-rings have not been used to carry RF current to a vibrating member in a high voltage circuit requiring minimal electrical resistance between its components. It is therefore surprising that a conductive O-ring is effective to provide the necessary electrical circuit to carry RF current in an ultrasonic surgical device.

SUMMARY OF THE INVENTION

In accordance with the present invention there is provided in a surgical apparatus for performing one or more surgical procedures at a surgical site on a patient comprising: a handpiece; a tool supported by said handpiece; said tool having a vibrating tool tip; vibrating means including a metal connecting member for ultrasonically vibrating said tool tip and RF current means selectively operable for providing an RF current to said tool tip for allowing performance of an electrosurgical procedure at the surgical site; said RF current means including switching means for switching the RF current provided to said tool tip to at least an RF cutting current during ultrasonic vibration, the improvement wherein said switching means comprises a switch module for selecting said RF current, an electrically conducting metal band connected to said switch module and an electrically conductive O-ring around said connecting member and in electrical contact with said metal band.

The conductive O-ring used in the improved surgical apparatus of the invention is made from a material which is commercially available, usually an elastomer impregnated with particles of electrically-conducting material, for example, silver coated aluminum. Conductive O-rings which have proved to be suitable are made from Parker Seals Compound #56410 available from Niantic Rubber Co., Cranston, R.I. and Compound #1285 available from Chomerics, Inc., Woburn, Mass.

In a preferred embodiment of the invention the tool tip has a tip opening and a tool passageway therethrough communicating with said tip opening, and the apparatus includes aspirating means for applying a suction pressure on said tool passageway for aspirating tissue particles and fluid at the surgical site through said tip opening through said tool passageway and away from the surgical site.

BRIEF DESCRIPTION OF THE DRAWINGS

The invention will be more particularly described with reference to a preferred embodiment as illustrated in the accompanying drawings, in which:

FIG. 1 is a side elevation, partly in section, of a surgical apparatus including the improved switching means of the invention;

FIG. 2 is an enlarged view of the section A defined by dotted lines in FIG. 1;

FIG. 3 is a side elevation of a conductive O-ring used in the switching means of the invention; and FIG. 4 is a section through the O-ring of FIG. 3.

DETAILED DESCRIPTION OF THE INVENTION

The apparatus illustrated in FIG. 1 of the drawings comprises a handpiece shown generally at 1 which is capable of performing ultrasonic fragmentation, aspiration, electrosurgical cutting, fluid irrigation, and electrosurgical coagulation or hemolysis functions on tissue at a surgical site on a patient. These functions may be performed either separately or simultaneously in any combination. The basic handpiece is preferably a known ultrasonic fragmentation handpiece such as that described in U.S. Pat. No. 4,063,557 or the above-mentioned CUSA handpiece, modified to include electrosurgical cutting and coagulating functions. These modifications can be built into the handpiece itself, or provided as part of a disposable or replaceable handpiece component such as on the manifold or nosecone thereof.

Handpiece 1 as shown in FIG. 1 comprises a plastic housing 2 and nose cone 3 sized and configured to be easily and comfortably gripped and manipulated by the surgeon's hand. The housing 2 accommodates an ultrasonic transducer 4 and the proximal end of an electrically conducting metal acoustic connecting member 5; and the housing 2 is threadably engaged to the nose cone 3 which accommodates the distal end of the connecting member 5 and the proximal end of an elongated tapered ultrasonically-vibratable tool 6. The tool, which also is made from an electrically-conducting metal, for example titanium, is threadably connected to the connecting member through a male thread 7. The tool 6 is disposed in a forward direction so that the tool tip 8 extends forwardly a distance out from the housing and has a tip opening 9 at its distal end. The tool is hollow and defines a longitudinal tool passageway therethrough.

An aspiration pump (not shown) can apply a suction pressure through tube 10 so that when the latter is connected to the proximal end 23 of the tool through conduit 11 tissue particles, blood, fluids and the like at a surgical site can be aspirated from the surgical site through the tool tip opening 9 and the tool passageway to be disposed in a suitable suction container (not shown).

One of the fluids which may be aspirated from the surgical site is a saline irrigation fluid provided thereto as part of the surgical procedure as for example to provide a suspension fluid for the tissue particles fragmented by the tool 6. The saline irrigation solution may drain by gravity in a known manner from a bottle or bag suspended above the surgical site through an irrigation tubing (not shown) to and into an appropriate inlet port in the handpiece. It then flows through an annular passage defined between the tool 6 and a plastic sleeve or manifold 12 surrounding the tool, and then out from the manifold around the tool tip 8 to the surgical site. In addition to supplying irrigation fluid to the surgical site, the fluid cools the vibrating tip 8 and adjacent healthy tissue is protected from damage. By mixing the fluid with the blood, tissue particles and other aspirated material coagulation of the blood is slowed down and aspiration thereof is aided. Where the surgical site is an enclosed or semienclosed area such as the eye in ultrasonic cataract removal procedures, it is important to maintain a pressure therein within a certain range, and flow control systems for maintaining such pressures are known, and can be used herein. See, for example, U.S. Pat. No. 3,693,613. Control of the delivery of irrigating fluid, and application of aspiration suction pressure and ultrasonic energy can be by a footswitch readily accessible to the surgeon as is known in the art.

The tool 6 is ultrasonically vibrated and is part of a resonant vibrating system mounted in the handpiece and comprising the connecting member 5 and transducer 4. The preferred transducer comprises a magnetostrictive stack as disclosed in U.S. Pat. No. Re. 25,033. The tool 6 preferably comprises a substantially unitary body having a male thread at its proximal end and is designed for replacement as required and attachment to the distal end of the connecting member 5. Preferably the ultrasonic resonator causes the tip 8 to vibrate ultrasonically with a stroke in excess of 0.001 inch and preferably 0.014 inch and at a frequency range of 20 KHz-50 KHz and preferably 23 KHz-37 KHz.

The electrosurgical unit (ESU) which provides the RF energy for the improved surgical apparatus of the invention may be a free standing hospital unit such as that disclosed in U.S. Pat. Nos. 3,898,991; 3,963,030 or 4,051,855 or, alternatively, it may be included in a single, preferably portable, unit within the same housing as the aspirator pump. The ESU generates RF energy and is operatively connected through a cable (not shown) to a switching means 13 on the nose cone 3 of the handpiece 1. Preferably, the ESU comprises a known type of electrical filtering device for preventing malfunction of the logic controls in the ESU when the ESU is activated while coupled, through the switching means, to the tool tip.

The switching means is positioned on the handpiece nose cone so as to be conveniently actuated by the surgeon as he manipulates the handpiece and it allows him to control the delivery of RF energy from the ESU to the tool 6. Thus, the switching means permits the surgeon to select from "no" RF energy, RF coagulating energy, RF cutting energy, and a blend of coagulating and cutting energies. RF cutting and coagulating currents differ and are defined as pure sine wave and damped sine wave, respectively.

The improved switching means of the present invention comprises a handswitch mounted on the nose cone of the handpiece so that it is accessible to and actuated by the surgeon's hand (for example, forefinger) as it holds and manipulates the handpiece.

A preferred embodiment of the handswitch is illustrated in FIG. 1 and comprises a separable and replaceable unit such as an add-on switch assembly attached to a separable handpiece manifold. Alternatively, the hand-switch may be integrally formed with or built into the housing of the handpiece so as to be totally re-usable (not shown). In all embodiments the switch module delivers RF energy to the connecting member of the apparatus through a conductive O-ring as herein described.

The switch assembly may be a push button, rocker or slide construction. A preferred embodiment is a rocker assembly as illustrated schematically in FIG. 1.

The rocker assembly permits the surgeon to select the "cut" mode of RF current from the ESU through normally open dome switches 14 or 15, respectively. When the relevant dome switch is closed the appropriate RF current is caused by a circuit board 16 (FIG. 2) in the switch module, to flow through a bifurcated, electrically conductive terminal 17, an electrically-conductive metal band 18 and an electrically-conductive O-ring 19 into the connecting member 5 and thence to the tool 6.

The electrically conductive O-ring 19 is preferably made from a rubbery elastomer impregnated or loaded with particles of an electrically-conductive material, such as silver-coated aluminum. For a standard ultrasonic surgical tool of the type described hereinabove the conductive O-ring 19 will normally have an internal diameter d (FIG. 3) of about 0.50 to 0.60 inch, preferably 0.56 inch and a cross-sectional diameter c (FIG. 4) of about 0.04 inch. When the nose cone 3 is tightened into locking engagement with the housing 2 the substantially circular cross section of the O-ring 19 is somewhat distorted as shown in figure 2. The resilience of the O-ring coupled with the tight fit allow the O-ring to maintain contact with the connecting member during operation thus avoiding any possibility of arcing. Likewise the contact between the metal band 18 and the O-ring 19 is maintained without arcing so that electrical continuity is sustained during operation of the apparatus. The metal band 18 is made from a ductile strip of electrically conductive metal, for example a beryllium copper alloy, having a thickness of about 0.004 to 0.005 inch. The width of the band is about 0.043 to 0.045 inch. The lower portion of the band is of substantially L-shape with the base of the L in touching contact with the O-ring 19. The upper portion of the band is bent over upon itself to form a springy plug which snaps into the bifurcated terminal 17 and maintains direct touching contact with the inside walls of the terminal at all times.

The connecting member is maintained in fluid-tight contact against housing 2 by a standard O-ring 20; and it is maintained in fluid-tight contact against nose cone 3 by a rearward O-ring 21 and a forward O-ring 22. The said O-rings are made of natural or synthetic rubber or a synthetic elastomeric polymer and are standard components in the art.

The forward O-ring 22 prevents irrigation fluid from entering the space surrounding the middle portion of the connecting member and the O-ring 20 prevents cooling liquid from entering the said space. The middle portion of the connecting member is defined herein as that portion which includes the electrical contact with the electrically conductive O-ring 19. Thus the said space is maintained as a substantially dry space and, consequently, there is no danger of liquid entering the switch module.

Repeated operations with an apparatus incorporating the improved switching means of the invention have resulted in substantially no deterioration in electrical efficiency. Examination of the conductive O-ring itself after numerous prolonged tests have shown no signs of burning or scorching due to arcing and substantially no mechanical deterioration.

What is claimed Is:

1. In a surgical apparatus for performing one or more surgical procedures at a surgical site on a patient comprising: a handpiece; a tool supported by said handpiece; said tool having a vibrating tool tip; vibrating means including a metal connecting member for ultrasonically vibrating said tool tip; and RF current means selectively operable for providing an RF current to said tool tip for allowing performance of an electrosurgical procedure at the surgical site; said RF current means including switching means for switching the RF current provided to said tool tip to at least an RF cutting current during ultrasonic vibration, the improvement wherein said switching means comprises a switch module for selecting said RF current, an electrically conducting metal band connected to said switch module and an electrically conductive O-ring around said connecting member and in electrical contact with said metal band.

2. An apparatus according to claim 1, in which said conductive O-ring is made from an elastomer impregnated with electrically-conducting particles of silver coated aluminum.

3. An apparatus according to claim 1, in which said electrically conducting metal band is connected to the switch module through an electrically conducting bifurcated terminal.

4. An apparatus according to claim 1, in which said tool tip has a tip opening and a tool passageway therethrough communicating with said tip opening, and the apparatus includes aspirating means for applying a suction pressure on said tool passageway for aspirating tissue particles and fluid at the surgical site through said tip opening through said tool passageway and away from the surgical site.

* * * * *